United States Patent [19]
McKee

[11] Patent Number: 5,363,052
[45] Date of Patent: Nov. 8, 1994

[54] PERMITTIVITY SPECTROSCOPY APPARATUS AND METHOD

[75] Inventor: James M. McKee, Reno, Nev.

[73] Assignee: Solid State Farms, Inc., Reno, Nev.

[21] Appl. No.: 18,230

[22] Filed: Feb. 16, 1993

[51] Int. Cl.$^5$ .......................... G01R 27/26
[52] U.S. Cl. .................. 324/663; 324/615; 324/633; 324/639
[58] Field of Search .............. 324/439, 612, 615, 629, 324/633, 634, 639, 640, 663, 664

[56] References Cited

U.S. PATENT DOCUMENTS

| | | | |
|---|---|---|---|
| 4,626,773 | 12/1986 | Kroeger et al. | 324/663 |
| 4,765,179 | 8/1988 | Fuller et al. | 73/53 |
| 4,767,982 | 8/1988 | Florig et al. | 324/640 |
| 5,132,623 | 7/1992 | De et al. | 324/639 X |

OTHER PUBLICATIONS

M. A. Stuchly and S. S. Stuchly, *Coaxial Line Reflection Methods for Measuring Dielectric Properties of Biological Substances at Radio and Microwave Frequencies—A Review*, IEEE Trans, Instru. Meas., vol. IM-19, No. 3, pp. 176–183, Sep. 1980.

K. C. Gupta, R. Garg, and I. J. Bahl, *Microstrip Lines and Slotlines*, RTech, pp. 2–4, (1979).

CRC Handbook of Chemistry and Physics, 67th ed., E50–56, CRC Press, 1986.

B. K. P. Scaife, Principle of Dielectrics—Monograms on the Physics and Chemistry of Material, p. 80, Clarendon Press (1989).

Primary Examiner—Kenneth A. Wieder
Assistant Examiner—Glenn W. Brown
Attorney, Agent, or Firm—Flehr, Hohbach, Test, Albritton & Herbert

[57] ABSTRACT

An apparatus and method for measuring the permittivity of a polar solution specimen to enable a determination of the concentration of polar constituents in the specimen. The apparatus (10) employs a band pass filter including containment means (18) formed to contain the polar solution (26) therein and electrically dispose the polar solution (26) as a dielectric element in the band pass filter; conducting means (12); a source of electrical current (56) connected to said band pass filter; frequency variation means (52) electrically connected to the electric voltage source (56) to enable variation of the frequency at which current is applied to the band pass filter; and voltage sensing means (52) electrically connected to sense the peak voltage passed by the band pass filter. The method includes providing a band pass filter having a conducting microstrip (12), disposing a specimen solution (26) between the conducting microstrip (12) and the ground plane 18); applying an electric current to the band pass filter; varying the frequency of the current; and determining the center frequency of the band pass filter as the current is varied.

14 Claims, 5 Drawing Sheets

PERMITTIVITY SPECTROSCOPY APPARATUS AND METHOD

TECHNICAL FIELD

This invention relates generally to permittivity spectroscopy, and more particularly, relates to measuring the dielectric constant of the specimen to enable a determination of the concentration of constituents in the specimen.

BACKGROUND ART

The measurement of the permittivity of high-loss polar liquids has historically proven to be a difficult task. Generally, the measurement of permittivity involves setting up a complex mechanical apparatus with very tightly controlled tolerances, carefully calibrating out electrical delays, and then inserting the specimen or sample. This is a time consuming process which is not readily adaptable to automation or a wide range of materials. Moreover it is susceptible to drifts in temperature of the sample, which degrade accuracy.

The measurement of the permittivity of aqueous solutions is difficult because of the high relative permittivity of water. One method for measuring permittivity is Time Domain Reflectrometry (TDR). In TDR, a fast rise time pulse is transmitted down a coaxial line until it intersects a test sample. The sample represents a discontinuity in the transmission line which causes a reflection. Measurement of the shape of the reflected pulse yields information which is a function of the reflection coefficient. From transmission line theory, the reflection coefficient is related to the characteristic impedance of the transmission line, from which the relative permittivity can be determined.

Although TDR is a widely used method for permittivity measurements (though not for aqueous solutions), it has numerous shortcomings. The sample-probe interface, for example, must have very close mechanical tolerances. As a result, TDR generally yields an accuracy of no better than two or three percent.

Another method of measuring permittivity is the Transmission Line Method (TLM) with a Network Analyzer (NWA). TLM is similar to TDR except that the NWA directly measures the reflection or transmission coefficient instead of deriving the coefficient from the shape of the waveforms. TLM is somewhat easier than TDR, however the same tight mechanical tolerances are required. With a large amount of fine tuning, accuracy of two to three percent is possible. Additionally, it is difficult to contain an aqueous sample in the transmission line without introducing spurious effects which degrade accuracy.

Most broadband permittivity measurements are made with the coaxial open-ended probe method. This is an ideal method for measuring the permittivity of polar liquids. A coaxial probe is simply placed against a sample, or in some cases into the liquid, and the changes in the reflection coefficient are measured by a NWA. These changes in reflection coefficient are measured as changes in the magnitude of the reflection coefficient and changes in the phase of the reflected signal. The sample permittivity can be calculated from the magnitude and phase of the reflection coefficient. However, the usefulness of this method is also limited to an accuracy of no better than one percent.

Many different types of coaxial open-ended probes are available. A summary of some of these techniques is found in an article by M. A. Stuchly and S. S. Stuchly, "Coaxial Line Reflection Methods for Measuring Dielectric Properties of Biological Substances at Radio and Microwave Frequencies—A Review," IEEE Trans. Instru. Meas., Vol. IM-29, no. 3, pp. 176-83, Sept. 1980.

The apparatus and method of the present invention provides a novel, highly accurate method of measuring the permittivity of aqueous solutions. Additionally, the present invention utilizes the concept of identification of compounds by measuring relaxation frequency using highly precise permittivity measurements. Large and complex molecules have low relaxation frequencies and small simple molecules have high relaxation frequencies. Therefore, if a solution has a mixture of molecules or compounds which have widely varying relaxation frequencies, and if those relaxation frequencies can be accurately measured, then the concentration of those different compounds in the solution can be determined.

DISCLOSURE OF THE INVENTION

In accordance with the illustrated preferred embodiment, the present invention provides an apparatus and method for measuring the concentration of constituents in a polar solution based upon a technique of measuring the permittivity of the solution using a microstrip circuit.

It is, therefore, an object of the present invention to provide a microstrip apparatus and method which are useful for determining the concentration of constituents in a polar solution.

Another object of the present invention is to provide a microstrip apparatus and method capable of determining the permittivity of a polar solution.

It is a further object of the present invention to provide a method and apparatus capable of determining permittivity with high accuracy and high resolution.

Still it is another object of the present invention to provide a method and apparatus useful for the determination of the concentration of constituents in a polar solution which is relatively economical to use, can be rapidly accomplished, and is suitable for use by relatively unskilled personnel.

The present invention has other objects and advantages which are set forth in the description of the Best Mode of Carrying Out the Invention. The features and advantages described in the specification, however, are not all inclusive, and particularly, many additional features and advantages will be apparent to one of ordinary skill in the art in view of the drawings, specification, and claims herein.

The above objects are achieved by employing an apparatus useful for determining the concentration of polar constituents in a polar solution. The apparatus employs a band pass filter including containment means formed to contain the polar solution therein and electrically dispose the polar solution as a dielectric element in the band pass filter; conducting means; a source of electrical current connected to said band pass filter; frequency variation means electrically connected to the electric voltage source to enable variation of the frequency at which current is applied to the band pass filter; and voltage sensing means electrically connected to sense the peak voltage passed by the band pass filter.

The method of the present invention includes, briefly, the steps of providing a band pass filter having a conducting microstrip, disposing a specimen solution between the conducting microstrip and the ground plane; applying an electric current to the band pass filter; varying the frequency of the current; and determining the center frequency of the band pass filter as the current is varied.

BEST MODE OF CARRYING OUT THE INVENTION

The present invention employs a microstrip method of permittivity measurement. The propagation of microwave signals through any microstrip circuit is a function of both the size and shape as well as the composition of the substrate. The present invention uses the sample or specimen under test to compose part of the substrate. Changes in the permittivity of the sample change the propagation characteristics of the electromagnetic fields. The changes in the propagation characteristics manifest themselves as a change in the characteristics of the microstrip circuit.

The preferred embodiment configures the microstrip to act as a band pass filter. Measured changes in the filter characteristics can be directly related to the substrate permittivity. The configuration comprising the preferred embodiment yields an accuracy of about 0.1% and the resolution of the permittivity approaches 0.02%.

FIGS. 1 through 4 and 7 of the drawings depict the preferred embodiment of the present invention for purpose of illustration only. One skilled in the art will readily recognize from the following discussion that alternative embodiments of the structures and methods illustrated herein may be employed without departing from the principles of the invention described herein.

The preferred embodiment of the present invention is an apparatus and method for determining the concentration of constituents in a polar solution based on the permittivity of the polar solution. As illustrated generally in FIG. 1, a microstrip assembly, generally designated 10, of the present invention includes a microstrip line (conducting means) 12, a substrate (non-conducting layer) 14, upper enclosure member 16, and lower enclosure or base member 18. Substrate 14 is fixed to lower enclosure 18 by fastening means such as screws 20, which pull down clamping members 19 against resilient sealing gasket members 21. The gaskets 21 are advantageously non-conductive. Upper enclosure 16 is attached to base 18 by fastening means, such as screws 22. A specimen or sample in the form of a polar solution 26 to be tested is placed in chamber 28, defined by substrate 14 and lower enclosure (containment means) 18, so that lower enclosure 18 contains solution 26.

Figure 1:
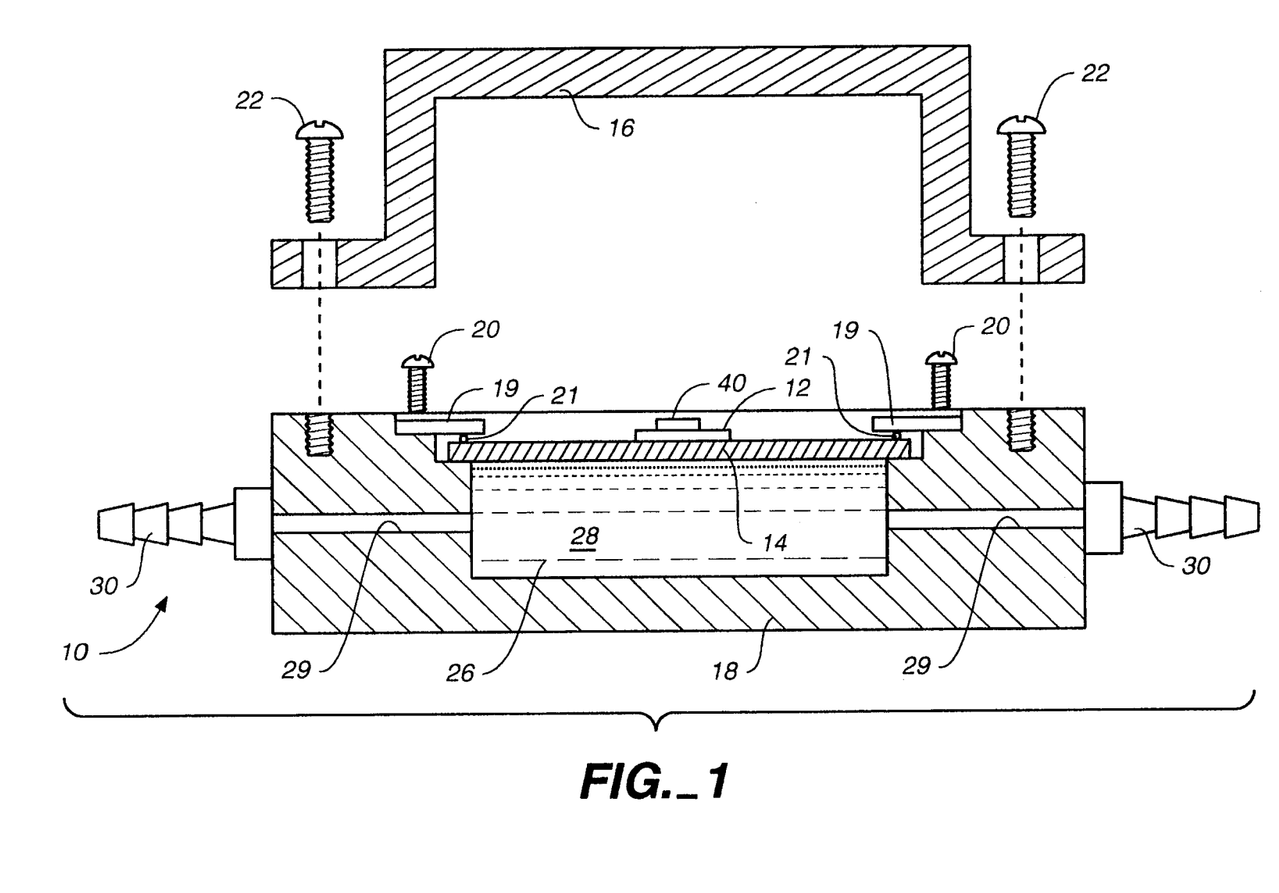
FIG. 1 is an exploded, side elevation view in cross section of a microstrip and specimen containment assembly constructed in accordance with the present invention.

Preferably, enclosures 16 and 18 are made of aluminum, and substrate 14 is made of a non-conducting material, such as alumina. Also, substrate 14 preferably is sufficiently thin that energy can pass from microstrip line 12 to base 18, and yet substrate 14 is sufficiently thick to support microstrip line 12. For example, substrate 14 can be provided by an alumina sheet about 0.25 inches thick.

Figure 2:
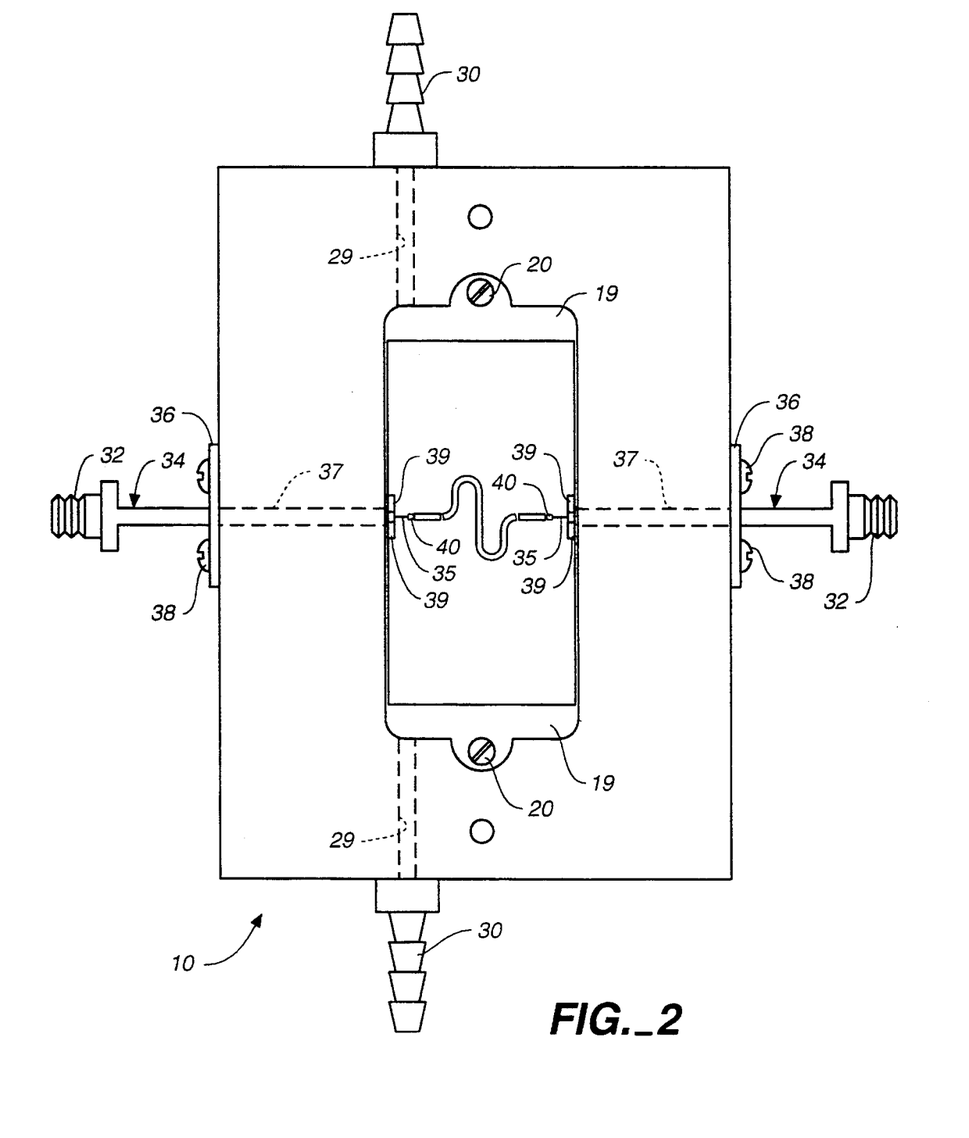
FIG. 2 is a cross-sectional top plan view of the microstrip assembly of FIG. 1.

FIG. 2 illustrates the permittivity sensor of the present invention with connections for the polar solution supply and electrical current but without upper enclosure 16 mounted on base 18. Polar solution 26 can be circulated into and out of chamber 28 via supply nozzles 30, which communicate with chamber 28 through bores or channels 29. Electrical connectors 32 (female SMA connectors) are attached to semi-rigid coaxial cables 34 that penetrate lower enclosure 18 just above substrate 14. Cables 34 extend through a hole in the center of plates 36 and base 18 into chamber 28. Plates 36 are fixed to base 18 by fasteners or screws 38. The shields 37 of cables 34 are peeled back to expose center conductor 35. Shields 37 are soldered at 39 to base 18 to provide a ground. Center conductors 35 of cables 34 are soldered to microstrip line 12 at leads 40.

Figure 3:
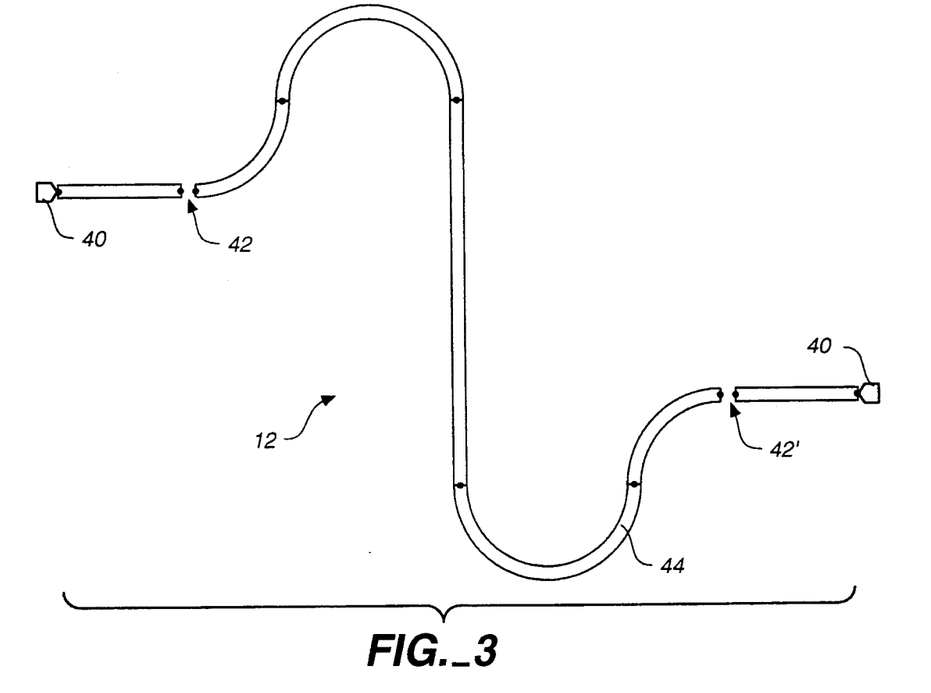
FIG. 3 is an enlarged, top plan view of the microstrip line.
Figure 4:
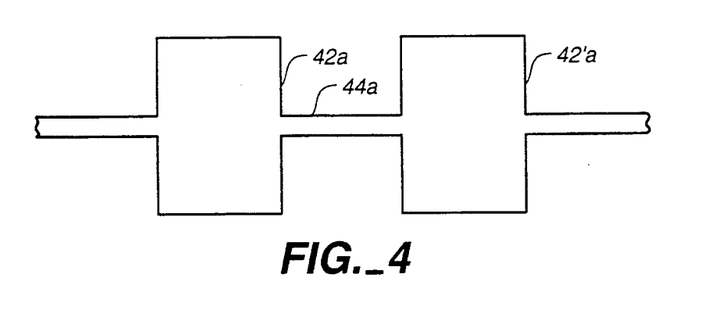
FIG. 4 is a top plan view of an alternate embodiment of the microstrip line.

Microstrip line 12 is fabricated using thick film technology using the smallest line thickness practicable. FIG. 3 shows the physical layout of microstrip line 12 as a band pass filter. It consists of a shunt capacitor 42, inductor 44 and shunt capacitor 42' in series.

Figure 5:
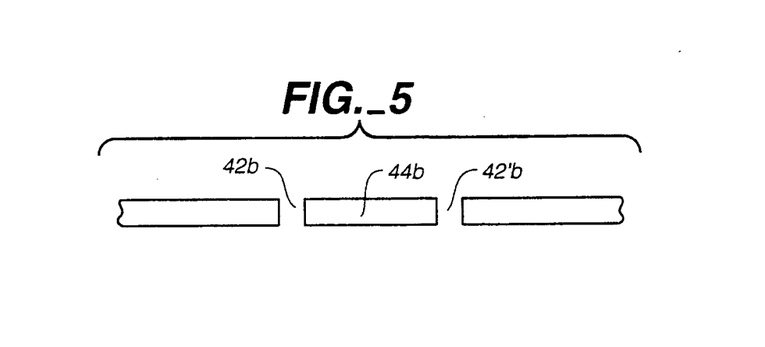
FIG. 5 is a top plan view of a further alternate embodiment of the microstrip line.
Figure 6:
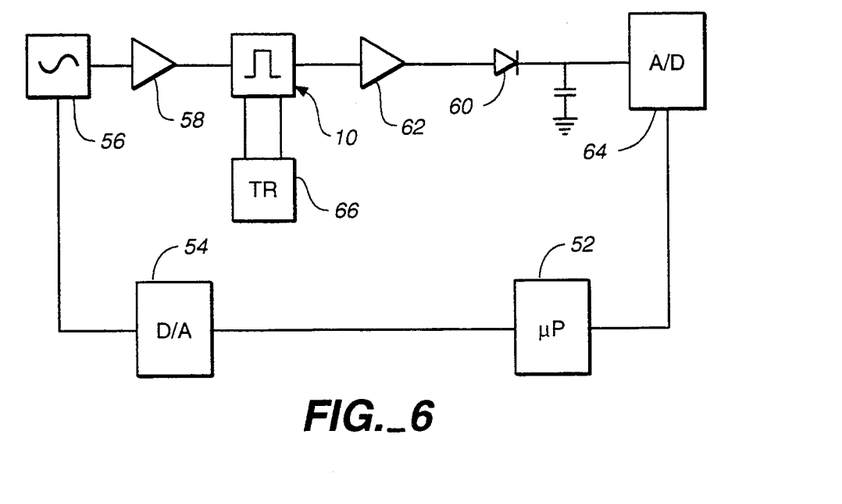
FIG. 6 is a block diagram of the overall electrical circuit used with the microstrip assembly of FIG. 1.

Microstrip 12 is not limited to the configuration shown in FIG. 3. Alternate configurations acting as a capacitor 42a, 42b, inductor 44a, 44b and capacitor 42'a, 42'b in series are shown in FIGS. 5 and 6. Additional configurations are also possible. Moreover, the microstrip line 12 may be configured to perform functions other than a band pass filter. Also, microstrip line 12 can be replaced by other microstrip techniques, such as slotline, coplanar waveguide, coplanar strips, inverted microstrip, suspended microstrip, microstrip with overlay, strip dielectric waveguide and inverted strip dielectric waveguide techniques. These alternate techniques are discussed in "Microstrip Lines and Slotlines," K. C. Gupta, R. Garg, and I. J. Bahl, RTech (1979). For the purposes of this disclosure, all of the above techniques are considered microstrip techniques. Thus, a microstrip assembly device or circuit may include any of the techniques discussed in the Gupta et al. reference. The configuration shown in FIG. 3 was chosen for the preferred embodiment due to its narrow band width.

In operation, polar solution 26 in concert with substrate 14 act as a dielectric element, and lower enclosure 18 acts as a ground plane. Upper enclosure 16 helps limit outside interference. Thus, microstrip line 12, substrate 14, polar solution 26, and lower enclosure 18 act in concert to create a microstrip circuit configured as a band pass filter. Energy from microstrip line 12 passes through substrate 14 and polar solution 26 (which acts as part of the substrate) to lower enclosure 18 (which acts as a ground plane).

Voltage source 56 supplies current to microstrip line 12 at leads 40. Only a band of frequencies are able to pass through the microstrip circuit. The frequency of the voltage from voltage source 56 is varied over a predetermined range by frequency variation means, such as an oscillator and computer controller. The range is determined by examining the relaxation frequencies and permittivities of the constituents. For example, using a prototype of the present invention to test a water and ethanol mixture at approximately 32° C. where water is the dominant constituent, a range of approximately 850 Mhz to 1000 Mhz is used, since the relaxation frequency for ethanol is approximately 900 Mhz, depending on temperature. The range for any compound should be near the relaxation frequency of one of the compounds. Alternately, a range near 10 GHz is also possible, since the relaxation frequency of water is approximately 18 GHz. The optimal range can be determined by experimentation or a computer model. The frequency at which the output voltage peaks corresponds to the center frequency of the band pass filter. The center frequency is used to determine the permittivity, since the center frequency is dependent on the permittivity of polar solution 26.

Figure 7:
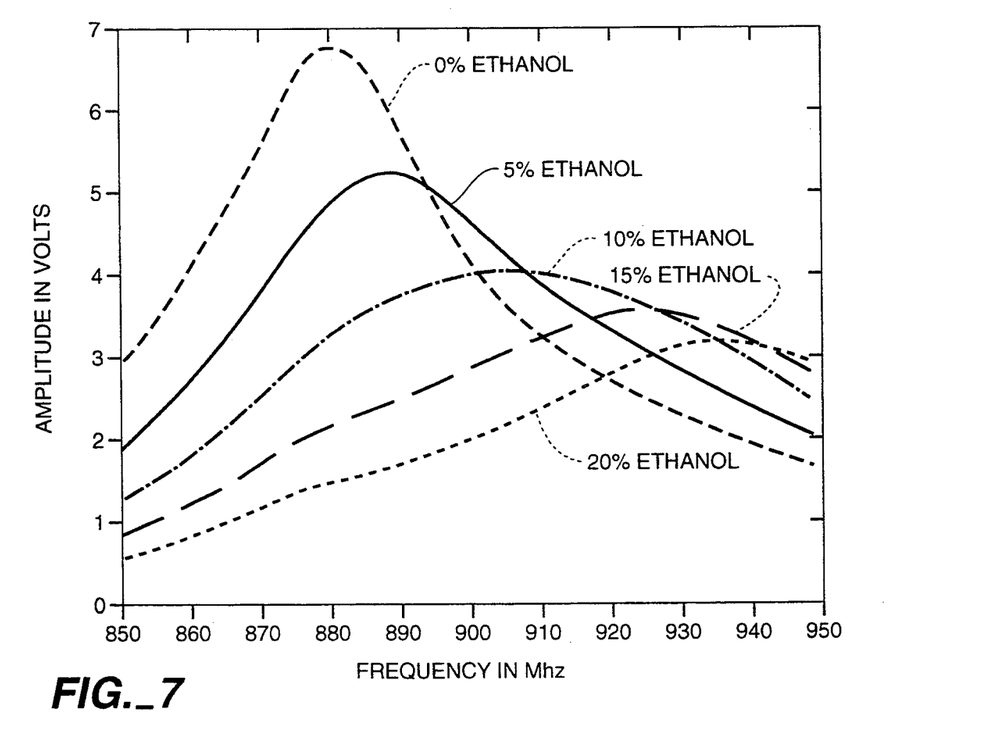
FIG. 7 is a graph of the raw data output from the overall electrical circuit used with the microstrip assembly of FIG. 1.

The physical layout for determining the center frequency is shown in FIG. 7 and includes computer 52, digital to analog (D/A) converter 54, voltage controlled oscillator 56, RF amplifier 58, microstrip assembly or circuit 10, video amplifier 62, diode detector circuit 60, analog to digital (A/D) converter 64, and temperature regulator 66. Under control of computer 52, a single frequency is produced, exciting microstrip circuit 10. The transmitted response of microstrip circuit 10 is amplified and rectified in diode detector circuit 60, and the output of diode detector circuit 60 is amplified and fed into A/D converter 64. The signal output from A/D converter 64 is fed to computer 52 and stored. Thus, computer 52 in concert with video amplifier 62, diode detector circuit 60 and A/D converter 64 act as a voltage sensing means. Computer 52, acting as a frequency variation means, then increments the frequency. The new output from microstrip circuit 10 is processed and stored in the same manner. This cycle is repeated until the entire frequency range selected is tested. Computer 52 also acts as calculation means and can calculate the concentration of the polar constituents by comparing the center frequency of solution 26 against calibration frequencies stored in the computer.

The power of the RF signal applied to microstrip line 12 is approximately 10 milliwatts into a 50 ohm system. Microstrip line 12 is made of a thick film conducting paste.

The permittivity of polar solution 26 and thus the center frequency, are also a function of temperature. Accordingly, the temperature of polar solution 26 in microstrip circuit 10 must be controlled. Temperature regulator (temperature control means) 66 performs this task. A pump (not shown) in temperature regulator 66 circulates polar solution 26 between microstrip assembly 10 and temperature regulator 66 via supply nozzles 30.

In practice, maintaining polar solution 26 at a constant temperature is a difficult task, even with temperature regulator 66. An alternative method for compensating for temperature drift is to calibrate microstrip circuit 10 for the temperature of polar solution 26. The center frequency is measured over a range of temperatures. An equation can be determined from these measurements to relate center frequency to temperature for any given solution.

To calibrate microstrip assembly 10 polar solution 26 is placed in a beaker and heated to 50° C. A water pump (not shown) circulates polar solution 26 through chamber 28 via nozzles 30. Additionally, a temperature sensor (not shown) is placed in chamber 28 and additional temperature sensors are placed in the beaker. Polar solution 26 is allowed to cool as it is circulated, until it reaches room temperature (20° C. to 25° C.). The center frequency is measured continuously through the cooling process to determine the relationship between temperature and center frequency.

The permittivity of a polar solution with known constituents of unknown concentration is determined from the center frequency by means of a predetermined formula. The permittivity formula is created by calibrating microstrip circuit 10 using known polar solutions of varying concentrations. These known solutions with known permittivities are tested to determine their center frequency. For example, the test solutions may be mixtures of water and ethanol, such as 0%, 5%, 10%, 15% and 20% ethanol and the balance water. Once the center frequency for each test solution is determined, corrections for temperature drift must be made using the calibration method described above. Of course, if a constant temperature is maintained for all center frequency measurements, this correction is not necessary.

The permittivities at a given temperature are known for the test solutions. These permittivities are found using reference tables, such as those found in the CRC Handbook of Chemistry and Physics, 67th ed., E50-56, CRC Press, 1986. These known permittivities may be used to plot the relationship between permittivity and the concentration of constituents in the test solution. Thus, for each test solution there are now three knowns: the concentration of constituents, the permittivity and the center frequency. Accordingly, the relationship between permittivity and frequency at a given temperature may be determined. This relationship serves as a general formula that may be applied to any test solution.

Figure 8:
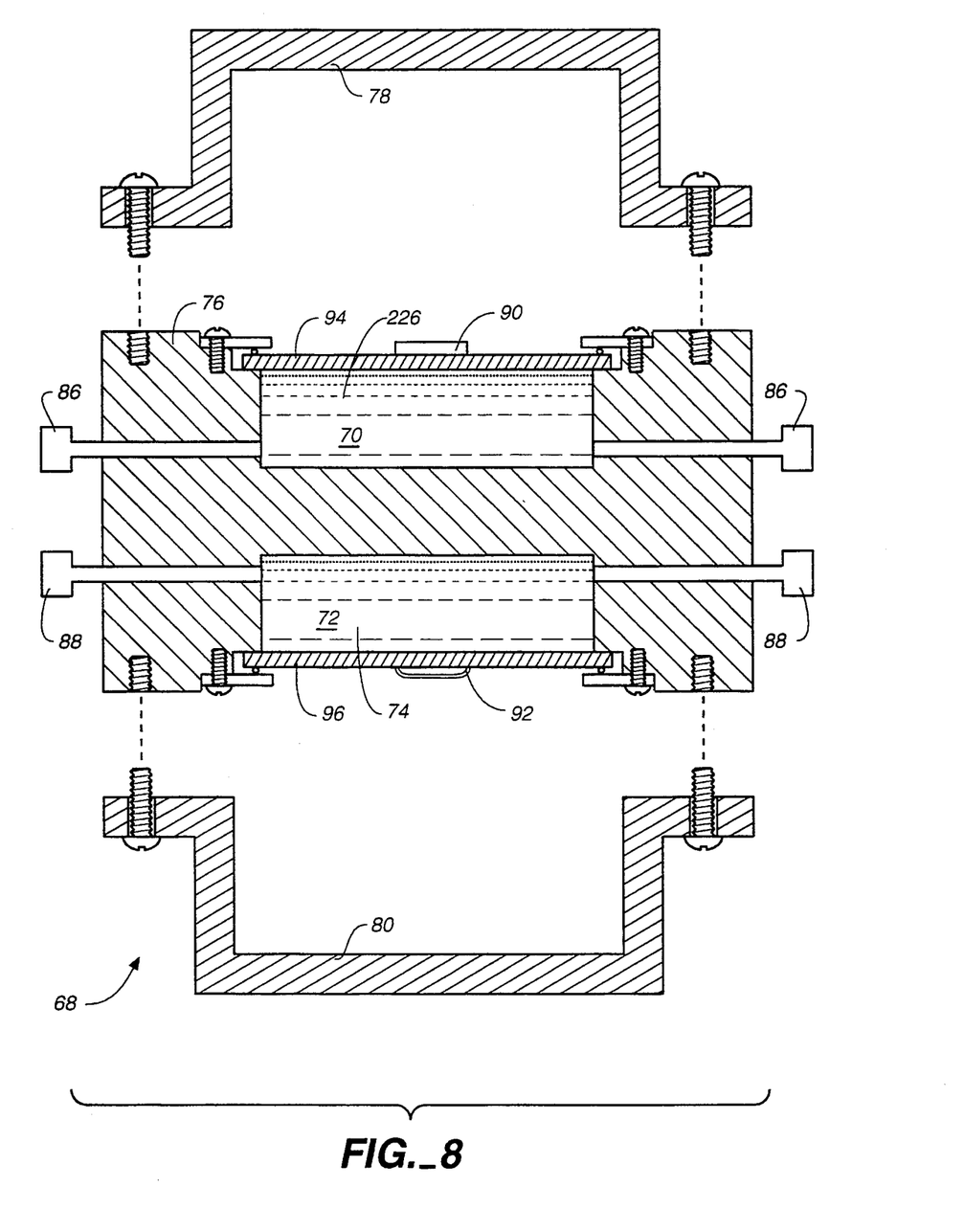
FIG. 8 is an exploded, side elevation view in cross section of still another alternate embodiment of the microstrip assembly.

To calibrate the prototype of the present invention, known test solutions of water and ethanol were used where the concentration of ethanol was varied from 0% to 20%. The raw data recorded by the microstrip circuit 10 consists of a bell-shaped curve of voltage amplitudes which represent the amount of energy passed at each frequency tested. The raw data collected is shown on FIG. 8. After correction for temperature effects as previously described, the frequencies corresponding to the peak amplitudes of each of the plots of the various percentages of ethanol may be related to the percentage of ethanol in the test solution. For the prototype, where frequency is measured in MHz, this relationship is linear and may be represented by the equation:

$$\text{Frequency} = 2.81 \times \text{percent ethanol} + 884.4 \text{ at a temperature of } 20°\text{ C.} \quad (1)$$

The known relationship between permittivity and the percent ethanol at 28° C. is represented by the equation:

$$\text{Permittivity} = -0.572 \times \%\text{ethanol} + 81.64 \quad (2)$$

The equation representing the relationship between frequency and percent ethanol may be rewritten as:

$$\%\text{ethanol} = (\text{frequency} - 884.4) \div 2.89 \quad (3)$$

Accordingly, the relationship between permittivity and frequency at 28° C. is as follows:

$$\text{Permittivity} = -0.197 \text{ (frequency} - 884.4) + 81.64 \quad (4)$$

This formula is useful for any polar solution under test at 28° C. for the prototype microstrip assembly of FIGS. 1–4 and 7. Since this formula is temperature dependent, all tests should be conducted at the calibration temperature corresponding to the formula.

The concentration of constituents may be determined from the measured permittivity of polar solution 26. The permittivity of any compound composed of multiple dielectric substances is a complex function of the percentages and permittivities of the various constituents. The most commonly used mixing model to describe the permittivity of solutions of polar liquids is:

$$\epsilon = (\epsilon_{sub1} \times \%\text{sub1}) + (\epsilon_{sub2} \times \%\text{sub2}) + (\epsilon_{sub3} \times \%\text{sub3}) + \ldots \quad (5)$$

This model is sufficient in most cases where the solution is dominated by one of the solutions (i.e., nearly pure). Other models exist describing the permittivity of complex solutions of various polar constituents, some of which factor in molecular level interactions. Many of these models are described in "Principle of Dielectrics—Monograms on the Physics and Chemistry of Material," p. 80, B. K. P. Scaife, Clarendon Press (1989), which is herein incorporated by reference.

If the temperature is fixed and the permittivity of the constituents differ substantially from each other, the above equation enables the present invention to determine the concentration of constituents in polar solution 26. If polar solution 26 contains a mixture of two polar liquids, the total permittivity $\epsilon_t$ of polar solution 26 is related to the permittivity and volume of the constituents by the following equation:

$$\epsilon_t = (\epsilon_{sub1}) \times (V_1) + (\epsilon_{sub2}) \times (V_2) \quad (6)$$

where $V_1$ and $V_2$ are the volume fractions of the two constituents. This equation can be reduced because $V_1 = 1 - V_2$. The reduced equation is:

$$V_1 = \frac{\epsilon_t - \epsilon_2}{\epsilon_1 - \epsilon_2} \quad (7)$$

where $\epsilon_1$ and $\epsilon_2$ are the permittivities of the constituents. Since $\epsilon_1$ and $\epsilon_2$ are known and $\epsilon_t$ is measured, $V_1$ can be determined. Thus, the concentrations of the constituents are calculable from the permittivity of polar solution 26.

It is also possible to calculate the concentration of constituents without calculating the permittivity of the test solution. This is done by calibrating microstrip circuit 10 using reference solutions with known concentrations of the same constituents as the test solution. The center frequency is determined for the reference solutions over a range of known concentrations of constituents to determine the relationship between concentration and center frequency. The center frequency of the test solution may then be measured using microstrip circuit 10. The tested center frequency can be compared to the known center frequencies of the reference solutions to determine the concentration of constituents in the test solution.

FIG. 9 shows an alternative embodiment of a microstrip assembly or circuit, generally designated 68. Instead of only one chamber 28 contained by lower enclosure or base 18, microstrip assembly 68 employs two chambers 70 and 72. Chamber 70 holds polar solution 26, and chamber 72 holds a known reference solution 74. Microstrip assembly 68 can be formed by placing two microstrip assemblies 10 (as shown in FIG. 1) bottom to bottom so that lower enclosures or base 18 abut each other. Alternatively, microstrip assembly 68 can have a single base or lower enclosure 76 with two chambers 70 and 72, and two upper enclosures 78 and 80. The two chambers 70 and 72 each require separate sets of electrical connectors (not shown), supply nozzles 86 and 88, microstrip lines 90 and 92, and substrates 94 and 96, respectively.

In operation, microstrip assembly 68 is center frequency/permittivity calibrated in the same manner described for the single chamber embodiment to determine a temperature dependent formula relating center frequency and total permittivity $\epsilon_t$. Reference solution 74 is preferably a pure polar liquid with known permittivity and corresponding to one of the constituents in polar solution 26. Reference solution 74 provides an alternate means for temperature calibrating microstrip assembly 68, which compensates for temperature drift problems efficiently, requiring minimal measurements.

The multi-chamber system allows microstrip assembly 68 to maintain both polar solution 26 and reference solution 74 at the same temperature. Prior to testing polar solution 26, the relationship between temperature and center frequency for reference solution 74 is determined in the same manner as discussed previously for microstrip circuit 10.

During the testing of polar solution 26, the center frequency of reference solution 74 is also determined. These measurements are carried out as close to the calibration temperature of the formula relating center frequency and total permittivity $\epsilon_t$ as possible. If the center frequency of reference solution 74 is different than as expected for the calibration temperature, there is a difference between the calibration temperature and actual temperature in chambers 70 and 72. This frequency difference is representative of the correction that must be made to the center frequency of polar solution 26. For example, if the center frequency of reference solution 74 is 10 Mhz more than expected, the center frequency of polar solution 26 should be reduced by 10 Mhz. The corrected frequency of polar solution 26 may then be used to calculate the permittivity and concentration of constituents in the same manner as discussed for microstrip circuit 10.

Microstrip circuits 10 and 68 may also be useful as temperature sensor devices. A calibration is performed using a known solution over a range of temperatures. During operation, if the same solution is in chamber 28, the center frequency may be translated into a temperature. For example, using distilled water, the center frequency of microstrip circuit 10 is related to the temperature by:

$$\ldots \text{Frequency} = 1.92 \times \text{Temperature} + 833.1 \quad (8)$$

where temperature is in °C. and frequency in MHz. Since the frequency can be measured to better than 1 KHz accuracy, temperature measurements with resolution and accuracy better than $5 \times 10^{-3}$° C. are realizable. The circuit can be placed in any type of enclosure for real time temperature measurement.

The present invention is useful beyond a two constituent polar solution. A mixture of three polar constituents can be analyzed by simultaneously measuring the permittivity at two frequencies. For a three constituent solution there exists a pair of frequencies for which the difference in permittivity measured at those frequencies is independent of the concentration of one of the three constituents. Permittivity is determined at the two frequencies and then subtracted from each other to yield a discriminator used to determine concentrations of one of the three constituents which make up the solution. The concentrations of the remaining two constituents are then determined using the method described above using the measured permittivity at one frequency. Additionally, models can be developed for polar solutions with greater than three constituents.

From the above description, it will be apparent that the invention disclosed herein provides a novel and advantageous apparatus and method useful for determining the concentration of constituents in a polar solution. The foregoing discussion discloses and describes merely exemplary methods and embodiments of the present invention. One skilled in the art will readily recognize from such discussion that various changes, modifications and variations may be made therein without departing from the spirit and scope of the invention. Accordingly, the disclosure of the present invention is intended to be illustrative, but not limiting, of the scope of the invention, which is set forth in the following claims.

We claim:

1. An apparatus useful for determining the concentration of polar constituents in a polar solution comprising:
   a microstrip circuit including containment means formed to contain said polar solution therein, and conducting means electrically disposed relative to said polar solution to couple said polar solution as a dielectric element in said microstrip circuit;
   a source of electrical current connected to said conducting means;
   frequency variation means electrically connected to said source to enable variation of the frequency at which current is applied to said conducting means; and
   voltage sensing means electrically connected to sense the peak voltage passed by said microstrip circuit.

2. The apparatus of claim 1, wherein said microstrip circuit is a band pass filter.

3. The apparatus of claim 2, wherein said band pass filter includes a first capacitor, an inductor, and a second capacitor electrically connected in series.

4. The apparatus of claim 1, wherein said conducting means is mounted on a non-conducting layer positioned between said solution and said conducting means, said layer forming a part of said dielectric element.

5. The apparatus of claim 1, wherein said containment means includes at least two chambers, with one of said at least two chambers containing said polar solution and the other of said at least two chambers containing a reference solution.

6. The apparatus of claim 1, further comprising:
   temperature control means coupled to said containment means for maintaining said solution at a constant temperature.

7. The apparatus of claim 1, wherein said conducting means is a microstrip line.

8. An apparatus for determining the concentration of polar constituents in a polar solution comprising:
   a microstrip band pass filter including containment means formed to contain said polar solution therein, and conducting means electrically disposed relative to said polar solution to couple said polar solution as a dielectric element in said microstrip band pass filter;
   a source of electrical current connected to said microstrip band pass filter;
   frequency variation means electrically connected to said source to enable variation of the frequency at which current is applied to said band pass filter;
   voltage sensing means electrically connected to sense the peak voltage passed by said band pass filter; and
   calculation means connected to said voltage sensing means and responsive thereto to calculate said concentration of said polar constituents.

9. The apparatus of claim 8, wherein said conducting means is a microstrip line.

10. The apparatus of claim 9, wherein said microstrip line includes a first capacitor, an inductor, and a second capacitor electrically connected in series.

11. The apparatus of claim 8, wherein said conducting means is mounted on a non-conducting support layer positioned between said solution and said conducting means.

12. The apparatus of claim 8, further comprising:
    temperature control means connected to said containment means and communicating with said solution to maintain said solution at a constant temperature.

13. The apparatus of claim 8, wherein said containment means includes at least two chambers, with one of said at least two chambers containing said polar solution and the other of said at least two chambers containing a reference solution.

14. An apparatus useful for determining the concentration of polar constituents in polar solutions comprising:
    an electrical component including a dielectric element in said electrical component;
    a source of electrical current connected to said electrical component;
    frequency variation means electrically connected to said source to enable variation of the frequency at which current is applied to said electrical component; and
    voltage sensing means electrically connected to sense the voltage passed by said electrical component.

* * * * *